United States Patent
Ballinari et al.

(10) Patent No.: US 9,119,877 B2
(45) Date of Patent: Sep. 1, 2015

(54) THERAPEUTIC COMBINATION COMPRISING A CDC7 INHIBITOR AND AN ANTI-NEOPLASTIC AGENT

(75) Inventors: Dario Ballinari, San Donato Milanese (IT); Antonella Ciavolella, Bizzarone (IT); Enrico Pesenti, Parabiago (IT); Alessia Montagnoli, Milan (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 518 days.

(21) Appl. No.: 13/509,625

(22) PCT Filed: Nov. 17, 2010

(86) PCT No.: PCT/EP2010/067675
§ 371 (c)(1),
(2), (4) Date: May 14, 2012

(87) PCT Pub. No.: WO2011/061222
PCT Pub. Date: May 26, 2011

(65) Prior Publication Data
US 2012/0276093 A1    Nov. 1, 2012

(51) Int. Cl.
*A61K 31/40*    (2006.01)
*A61K 31/495*   (2006.01)
*A61K 45/06*    (2006.01)
*A61K 31/506*   (2006.01)

(52) U.S. Cl.
CPC ............... *A61K 45/06* (2013.01); *A61K 31/40* (2013.01); *A61K 31/495* (2013.01); *A61K 31/506* (2013.01)

(58) Field of Classification Search
CPC .................... A61K 31/40; A61K 31/495
USPC .................................................. 514/275
See application file for complete search history.

(56) References Cited

U.S. PATENT DOCUMENTS 5,750,737 A * 5/1998 Sisti et al. ............... 549/510

FOREIGN PATENT DOCUMENTS

WO    WO 2007/110344 A1    10/2007
WO    WO 2009/133170 A1    11/2009

* cited by examiner

*Primary Examiner* — Yong Chong
(74) *Attorney, Agent, or Firm* — Scully, Scott, Murphy & Presser, P.C.

(57) ABSTRACT

The present invention provides a therapeutic combination comprising (a) a compound of formula (I) as set forth in the specification and (b) one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent, a proteasome inhibitor, an inhibitor of an anti-apoptotic protein and an antibody directed against a cell surface protein, wherein the active ingredients are present in each case in lice form or in the form of a pharmaceutically acceptable salt or any hydrate thereof.

4 Claims, No Drawings

THERAPEUTIC COMBINATION COMPRISING A CDC7 INHIBITOR AND AN ANTI-NEOPLASTIC AGENT

TECHNICAL FIELD

The present invention relates in general to the field of cancer treatment and, more particularly, provides an antitumor composition comprising a Cdc7 inhibitor and one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent, a proteasome inhibitor, an inhibitor of an anti-apoptotic protein and an antibody directed against a cell surface protein, having a synergistic or additive antineoplastic effect.

BACKGROUND ART

Cdc7 is a serine/threonine kinase that promotes DNA replication origin firing by phosphorylating one or more subunits of the MCM DNA helicase complex (Mcm2-7), thus leading to the unwinding of double-stranded DNA at origins of replication. Like cyclin dependent kinases, Cdc7 activity requires the binding of either one of two regulatory subunits, Dbf4 and Drf1/Dbf4B. Periodic accumulation of Cdc7, Dbf4 and Drf1/Dbf4B during S-phase is thought to be the major mechanism that regulates Cdc7 activity during the cell cycle.

Cdc7 depletion through RNA interference causes tumor cells to enter apoptosis in a p53 independent manner, while simply arresting cell cycle progression in normal cells, Furthermore, Cdc7 is a downstream target of the replication checkpoint proteins ATR and Chk2 and it is therefore not only an essential cell cycle regulator but also important for genome integrity in response to DNA damage. As a consequence, Cdc7 depletion in the presence of topoisomerase inhibitors or intercalating agents, increases cell death.

Altered expression of proteins involved in the initiation of DNA replication closely correlates with aggressive phenotypes and is a powerful marker of clinical outcome in a variety of malignancies. Cdc7 levels are increased in many cancer cell lines and primary tumors, such as breast, lung, ovary and melanoma cancers, compared to matched normal tissues and correlate with poor prognosis. Furthermore, somatic CDC7 mutations have been identified in colorectal and gastric carcinomas through comprehensive kinome screens of human tumors, DBF4 is also considered as a novel determinant in cutaneous melanoma development with prognostic relevance and it is also found to be amplified in some tumor cell lines and primary tumors, such as colon, lung and ovary.

These findings suggest that alterations in Cdc7/Dbf4 protein abundance or activity may occur during tumorigenesis and have important consequences for cell survival.

Drugs that target DNA replication elongation are widely used in chemotherapy, for example, gemcitabine, active metabolites of 5-fluorouracil and hydroxyurea, topoisomerase inhibitors, or DNA intercalating agents. A blockade of replication forks often results in breakage of the DNA molecules, and in the activation of an ATR/ATM dependent S-phase checkpoint pathway that senses the damage and mediates cellular responses to drug treatment. In contrast, Cdc7 inhibition prevents the activation of replication origins but does not trigger a sustained activation of the DNA damage response and a cell cycle block but rather induces apoptosis.

Some heteropentacycles have been demonstrated to be potent inhibitors of Cdc7 and are thus useful in the treatment of the proliferative disorders, especially cancer. One of these compounds is currently in development as an anti-cancer agent.

There is a continuous need of anticancer agents in order to optimise the therapeutic treatment. The present invention fulfils this need by providing new combinations of a Cdc7 inhibitor with known pharmaceutical agents that are particularly suitable for the treatment of proliferative disorders, especially cancer. More specifically, the combinations of the present invention are very useful in therapy as antitumor agents and lack, in terms of both toxicity and side effects, the drawbacks associated with currently available antitumor drugs.

DESCRIPTION OF THE INVENTION

The present invention provides, in a first aspect, a therapeutic combination comprising (a) a compound of formula (I):

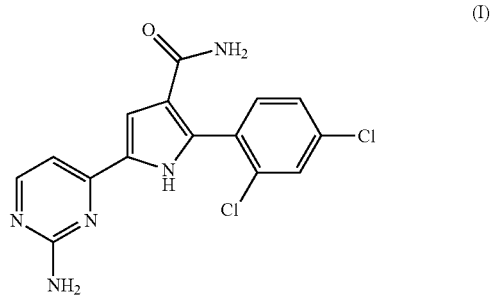

and (b) one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent, a proteasome inhibitor, an inhibitor of an anti-apoptotic protein and an antibody directed against a cell surface protein wherein the active ingredients are present in each case in free form or in the form of a pharmaceutically acceptable salt or any hydrate thereof.

The present invention also provides a combined preparation for simultaneous, separate or sequential use of the combination as described above.

In a further aspect the invention relates to the combination according to the invention for use in a method of treating or delaying the progression of a proliferative disorder, wherein the said method comprises the simultaneous, sequential or separate administration to a subject in need thereof of the therapeutic combination.

In a still further aspect the invention provides a pharmaceutical composition comprising a combination according to the invention admixed with a pharmaceutically acceptable carrier, diluent or excipient.

A still further aspect relates to the use of a compound of formula (I) as defined above in the preparation of a medicament for the treatment of a proliferative disorder, wherein said treatment comprises simultaneously, sequentially or separately administering a compound of formula (I) as defined above and one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent, a proteasome inhibitor, an inhibitor of an anti-apoptotic protein and an antibody directed against a cell surface protein, to a subject.

Another aspect relates to the use of a compound of formula (I) as defined above and one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent, a proteasome inhibitor, an inhibitor of an anti-apoptotic protein and an antibody directed against a cell surface protein, in the preparation of a medicament for treating a proliferative disorder.

The compound of formula (I) has the chemical name 5-(2-Amino-pyrimidin-4-yl)-2-(2,4-dichloro-phenyl)-1H-pyrrole-3-carboxylic acid amide. The preparation of this compound is described in WO2007110344 (Nerviano Medical Sciences S.r.I.); in particular, it can be prepared as free base form according to the synthetic procedure of example 19, step 3 of WO2007110344. An alternative process for its preparation is described in the co-pending International Patent Application number PCT/EP2009/055262, filed the name of the present applicant on Apr. 30, 2009.

Pharmaceutically acceptable salts of the compound of formula (I) include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

According to a preferred embodiment of the invention, the alkylating or alkylating-like agent is selected from the group consisting of nitrogen mustards (mechlorethamine, cyclophosphamide, ifosfamide, melphalan and chlorambucil), aziridines (thiotepa), nitrosoureas (carmustine, lomustine, semustine), triazenes (dacarbazine and temozolomide) and platinum derivatives (cisplatin, oxaliplatin, carboplatin and satraplatin). Cisplatin can be administered, e.g., in the form as it is marketed, e.g. under the trademark CDDP®. Temozolomide can be administered, e.g., in the form as it is marketed, e.g. under the trademark TEMODAR®. Dacarbazine can be administered, e.g., in the form as it is marketed, e.g. under the trademark DTIC.

According to a more preferred embodiment of the invention, the alkylating or alkylating-like agent is cisplatin.

An antimetabolite agent includes, but is not limited to, 5-fluorouracil, capecitabine, gemcitabine, pemetrexed, methotrexate, fludarabine and edatrexate. Capecitabine can be administered, e.g., in the form as it is marketed, e.g. under the trademark XELODA Gemcitabine can be administered, e.g., in the form as it is marketed, e.g. under the trademark GEMZAR Pemetrexed can be administered, e.g., in the form as it is marketed, e.g. under the trademark ALIMTA®. Fludarabine can be administered, e.g., in the form as it is marketed, e.g. under the trademark FLUDARA®.

A topoisomerase I inhibitor includes, but is not limited to, topotecan, irinotecan (CPT-11), SN-38 and 9-nitrocamptothecin, Innotecan can be administered, e.g., in the form as it is marketed, e.g. under the trademark CAMPTOSAR ®. Topotecan can be administered, e.g., in the form as it is marketed, e.g, under the trademark HYCAMTIN®.

A topoisomerase II inhibitor includes, but is not limited to, anthracyclines (doxorubicin, daunorubicin, epirubicin, nemorubicin and idarubicin), podophillotoxins (etoposide and teniposide), anthraquinones (mitoxanthrone and losozanthrone) and acridines (actinomycin D, bleomycin and mitomycin). Etoposide can be administered, e.g., in the form as it is marketed, e.g. under the trademark EPOSIN®.

An inhibitor of a growth factor or of a growth factor receptor can be an antibody or a low molecular weight chemical compound. The former includes, but it is not limited to, bevacizumab and cetuximab; the latter includes, but it is not limited to, erlotinib and gefitinib. Bevacizumab can be administered, e.g., in the form as it is marketed, e.g, under the trademark AVASTIN®. Cetuximab can be administered, e.g., in the form as it is marketed, e.g. under the trademark ERBITX®. Erlotinib can be administered, e.g., in the form as it is marketed, e.g. under the trademark TARCEVA®. Gefitinib can be administered, e.g., in the form as it is marketed, e.g. under the trademark IRESSA®.

An antimitotic agent includes, but it is not limited to, taxanes (paclitaxel and docetaxel). Paclitaxel can be administered, e.g., in the form as it is marketed, e.g. under the trademark TAXOL®.

A proteasome inhibitor includes, but it is not limited to, Bortezomib. Bortezomib can be administered, e.g., in the form as it is marketed, e.g. under the trademark VELCADE®.

An inhibitor of anti-apoptotic proteins includes, but it is not limited to the Bcl-2 inhibitor Navitoclax (ABT-263).

An antibody directed against a cell surface protein includes, but it is not limited to, anti-CD20 monoclonal antibodies such as rituximab, ibritumomab, tiuxetan, tositumomab and ofatumumab. Rituximab can be administered, e.g., in the form as it marketed, e.g., under the trademark RITUXAN®, In the present invention, each of the active ingredients of the combination is in amount effective to produce a synergic antineoplastic effect.

The present invention also provides a method for lowering the side effects caused by antineoplastic therapy with an antineoplastic agent in mammals, including humans, in need thereof, the method comprising administering to said mammal a combined preparation comprising the compound of formula (I) as defined above and one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent and a proteasome inhibitor, in amounts effective to produce a synergic antineoplastic effect.

By the term "a synergic antineoplastic effect" as used herein is meant the inhibition of the growth tumor, preferably the complete regression of the tumor, by administering an effective amount of the combination of a the compound of formula (I) as defined above and an alkylating or alkylating-like agent, an antimetabolite agent, a topoisomerase I inhibitor, a topoisomerase II inhibitor, an inhibitor of a growth factor or of a growth factor receptor, an antimitotic agent or a proteasome inhibitor to mammals, including human.

The term "combined preparation" as used herein defines especially a "kit of parts"in the sense that the combination partners (a) and (b) as defined above can be dosed independently or by use of different fixed combinations with distinguished amounts of the combination partners (a) and (b), i.e. simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

By the term "administered" or "administering" as used herein is meant parenteral and /or oral administration. By "parenteral" is meant intravenous, subcutaneous and intramuscolar administration.

In the method of the subject invention, for the administration of the compound of formula (I), the course of therapy generally employed is in the range from 1 mg/m2 to 0.5 g/m2 as free base. More preferably, the course therapy employed is from about 20 mg/m2/day to about 200 mg/m2/day as free base. Typical regimens comprises the following administration schedules; daily for up to 21 consecutive days; daily for 7 consecutive days, followed by a rest period of one week for a total of 14-day cycle (two-weeks cycle).; daily for 14 days, followed by a rest period of one week (three-weeks cycle); daily on days 1 to 7 and 15 to 21 of a four-weeks cycle.

The compound of formula (I) can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

In the method of the subject invention, for the administration of an alkylating agent, preferably temozolomide, the course of therapy generally employed is from 15 mg/m$^2$ to 300 mg/m$^2$ daily. More preferably, the course of therapy generally employed is from about 50 mg/m$^2$ to 150 mg/m$^2$ daily for up to 42 consecutive days.

For the administration of a platinum derivative, preferably cisplatin, the course of therapy generally employed is from 10 mg/m$^2$/day to 100 mglm$^2$/day every 2-4 weeks. More preferably, the course of therapy generally employed is from about 50 mg/m$^2$ to 100 mg/m$^2$ on day 1, once every 3-4 weeks.

For the administration of a platinum derivative, preferably carboplatin, the course of therapy generally employed depends on the systemic exposure (expressed as AUC value), the renal function of the patient and on the schedule of administration. A regimen targeting an AUC of from 4 to 6 mg/mi./min over a 2 to 4 week schedule is usually adopted. More preferably, a regimen targeting an AUC of 5 mg/mUmin over a 4-week schedule is used.

For the administration of an antimetabolite agent, preferably gemcitabine or pemetrexed, the course of therapy generally employed is from 200 mg/m$^2$ to 2000 mg/m$^2$ as weekly administration. More preferably, the course of therapy generally employed is from about 500 mg/m$^2$ to 1250 mg/m$^2$ on days 1 and 8 of a 21-days cycle or on days 1, 8, 15 of a 28-day cycle (gemcitabine) or on days 1 of a 21-day cycle (pemetrexed).

For the administration of an antimetabolite agent, preferably fludarabine, the course of therapy generally employed is from 15 mg/m$^2$ to 40 mg/m$^2$ as daily administration. More preferably, the course of therapy generally employed is about 25 mg/m$^2$ on days 1 to 5 of a 28-days cycle.

For the administration of a topoisomerase I inhibitor, preferably irinotecan, the course of therapy generally employed is from 35 mg/m$^2$ to 350 mg/m$^2$ on days 1, 8, 15, 22 of a 42-day cycle or on days 1,15, 29 of a 42-day cycle or on day 1 of a 21-day cycle. More preferably, the course of therapy generally employed is 125 mg/m$^2$ on days 1, 8, 15, 22 and 29 of a 42-day cycle.

For the administration of a topoisomerase II inhibitor, preferably etoposide, the course of therapy generally employed is from 10 mg/m$^2$ to 200 mg/m$^2$ daily, preferably from 35 to 100 mg/m$^2$ daily, for 3 to 5 days of a 21 or 28-day cycle or on days 1, 3, 5 of a 21 or 28-day cycle. These dosages are intended for IV administration; in case of oral administration doses are doubled.

For the administration of an inhibitor of a growth factor receptor, preferably erlotinib, the course of therapy generally employed is from 10 to 1000 mg daily. More preferably, the course of therapy generally employed is 100-150 mg daily For the administration of an inhibitor of a growth factor receptor, preferably bevacizumab, the course of therapy generally employed is from 0.1 mg/m2 to 100 mg/m2 on day 1 of a 14-day cycle or 21-day cycle. More preferably, the course of therapy generally employed is from 1 to 20 mg/m2 on day 1 of a 14-day cycle or 21-day cycle.

For the administration of an antimitotic agent, preferably paclitaxel, the course of therapy generally employed is from 50 mg/m$^2$ to 175 mg/m$^2$ on day 1 of a 14 or 21-day cycle or from 30 mg/m2 weekly. More preferably, the course of therapy generally employed is 175 mg/m2 on day 1 of a 21-day cycle For the administration of a proteasome inhibitor, preferably bortezomib, the course of therapy generally employed is 0.1 mg/m2 to 30 mg/m2 every three weeks.

For the administration of an inhibitor of an anti-apoptotic protein, preferably Navitoclax (ABT-263), the course of therapy employed has no precise standards and depends on, among other factors, the disease to be treated and the conditions of the patient.

For the administration of an antibody directed against a cell surface protein, preferably rituximab, the course of therapy generally employed is from 50 mg/m$^2$ to 1000 mg/m$^2$ as weekly administration. More preferably, the course of therapy generally employed is from about 250 to 500 mg/ m$^2$, more preferably 375 mg/m$^2$ on day 1 of a 7-days cycle, The antineoplastic therapy of the present invention is in particular suitable for treating all form of cancer including, but not limited to: carcinoma such as bladder, breast, colon, kidney, liver, lung, including small cell lung cancer, oesophagus, gall- bladder, ovary, pancreas, stomach, cervix, thyroid, prostate, and skin, including squamous cell carcinoma; haematopoietic tumors of lymphoid lineage including leukaemia, acute lymphocytic leukaemia, acute lymphoblastic leukaemia, chronic lymphocytic leukaemia, B-cell lymphoma, T-cell-lymphoma, Hodgkin's lymphoma, non-Hodgkin's lymphoma, hairy cell lymphoma and Burkett's lymphoma, multiple myeloma; haematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; mesothelioma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

As stated above, the effect of the combination of the invention is significantly increased without a parallel increased toxicity. In other words, the combined therapy of the present invention enhances the antitumoral effects of the partner (a)

and/or of partner (b) of the combination of the invention and thus yields the most effective and less toxic treatment for tumors.

Pharmaceutical compositions according to the invention are useful in anticancer therapy.

The present invention further provides a commercial package comprising, in a suitable container mean, (a) a compound of formula (I) as defined above, and (b) one or more antineoplastic agents selected from the group consisting of an alkylating or alkylating-like agent, an antimetabolite agent, a topoisomerase I inhibitor, a topoisomerase II inhibitor, an inhibitor of a growth factor or of a growth factor receptor, an antimitotic agent and a proteasome inhibitor, wherein the active ingredients are present in each case in free form or in the form of a pharmaceutically acceptable salt or any hydrate thereof, together with instructions for simultaneous, separate or sequential use thereof.

In a package according to the invention each of partner (a) and (b) are present within a single container mean or within distinct container means.

Another embodiment of the present invention is a commercial package comprising a pharmaceutical composition or product as described above.

Due to the key role of the cdc7 protein in the regulation of cellular proliferation, the combinations of the present invention are also useful in the treatment of a variety of cell proliferative disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

The combinations of this invention, as modulators of apoptosis, may also be useful in the treatment of cancer, viral infections, prevention of AIDS development in HIV-infected individuals, autoimmune diseases and neurodegenerative disorders.

The activities of the combination of the present invention are shown for instance by the following in vitro and in vivo tests, which are intended to illustrate but not to limit the present invention,

EXAMPLES

Materials and methods. Exponentially growing human breast cancer (Mcf-7), human ovarian cancer (A-2780), human multiple myeloma (L-363), human colorectal cancer (HCT-116) and human melanoma (A-375) cell lines were seeded and incubated at 37° C. in a humidified 5% $CO_2$ atmosphere. Drugs were added to the experimental culture, and incubations were carried out at 37° C. for 72 hours in the dark. Scalar doses of the compound of formula (I) and antineoplastic agents were added to the medium starting from 24 hours after seeding. Drug solutions were prepared immediately before use. At the end of treatment, cell proliferation was determined by an intracellular adenosine triphosphate monitoring system (CellTiterGlo-Promega) using an Envision (PerkinElmer) reader. Inhibitory activity was evaluated comparing treated versus control data using the Assay Explorer (MDL) program. The dose inhibiting 50% of cell growth was calculated using sigmoidal interpolation curve. Combination indices (C.I.) were calculated using a proprietary computer program for multiple drug effect analysis based on the equation of Chou-Talalay (Adv Enzyme Regul 1984;22:27-55) for mutually nonexclusive drugs, where a C.I. of <1 indicates a more than additive effect: C.I.: >3 strong antagonism; 1.3-3 antagonism; 1.2-0.8 additivity; 0.8-0.3 synergism; <0.3 strong synergism.

Example 1

In vitro Cytotoxic Activity of the Combination with Gemcitabine

The results obtained with the drugs as single agents and in combination in the Mcf-7 human breast adenocarcinoma cell line are shown in Table 1.

TABLE 1

| | in vitro combination with gemcitabine | | | | | |
|---|---|---|---|---|---|---|
| Ratio | $IC_{50}$ (μM) Compound of formula (I) | $IC_{50}$ (μM) Gemcitabine | $IC_{50}$ (μM) Combination | Combination index at 50% inhibition | Combination index at 70% inhibition | Schedule |
| 2.5:1 | 1.10 | 0.79 | 0.23 | 0.24 | 0.36 | Sequential: gemcitabine 24 hours before compound of formula (I) |
| 1.25:1 | 1.10 | 0.79 | 0.42 | 0.49 | 0.40 | Sequential: gemcitabine 24 hours before compound of formula (I) |
| 0.625:1 | 1.10 | 0.79 | 0.40 | 0.50 | 0.37 | Sequential: gemcitabine 24 hours before compound of formula (I) |
| 5:1 | 1.10 | 0.79 | 0.27 | 0.28 | 0.31 | Sequential: gemcitabine 24 hours before compound of formula (I) |

The results show that on human tumor cells compound of formula (I) can be effectively combined with the antimetabolite agent gemcitabine producing synergic or strong synergic effect.

Example 2

In vitro Cytotoxic Activity of the Combination with Cisplatin

The results obtained with the drugs as single agents and in combination in Mcf-7 cell line are shown in table 2.

TABLE 2 in vitro combination with cisplatin

| Ratio | $IC_{50}$ (μM) Compound of formula (I) | $IC_{50}$ (μM) cisplatin | $IC_{50}$ (μM) Combination | Combination index at 50% inhibition | Combination index at 70% inhibition | Schedule |
|---|---|---|---|---|---|---|
| 0.05:1 | 1.7 | 10.2 | 2.19 | 0.28 | 0.53 | Sequential: cisplatin 24 hours before compound of formula (I) |
| 0.025:1 | 1.7 | 10.2 | 2.94 | 0.33 | 0.60 | Sequential: cisplatin 24 hours before compound of formula (I) |
| 0.012:1 | 1.7 | 10.2 | 5.97 | 0.65 | 0.31 | Sequential: cisplatin 24 hours before compound of formula (I) |
| 0.1:1 | 1.7 | 10.2 | 2.54 | 0.39 | 0.51 | Sequential: cisplatin 24 hours before compound of formula (I) |

The results show that on human tumor cells compound of formula (I) can be effectively combined with platinum-containing compound cisplatin, producing synergic or strong synergic effect.

Example 3

In vitro Cytotoxic Activity of the Combination with Cisplatin

The results obtained with the drugs as single agents and in combination in the A2780 human ovarian carcinoma cellline are shown in Table 3.

TABLE 3 in vitro combination with cisplatin

| Ratio | $IC_{50}$ (μM) Compound of formula (I) | $IC_{50}$ (μM) cisplatin | $IC_{50}$ (μM) Combination | Combination index at 70% inhibition | Combination index at 90% inhibition | Schedule |
|---|---|---|---|---|---|---|
| 0.1:1 | 0.52 | 3.0 | 1.27 | 0.54 | 0.46 | simultaneous |
| 0.2:1 | 0.52 | 3.0 | 1.14 | 0.66 | 0.58 | simultaneous |
| 0.4:1 | 0.52 | 3.0 | 0.90 | 0.63 | 0.52 | simultaneous |
| 0.8:1 | 0.52 | 3.0 | 0.71 | 0.67 | 0.58 | simultaneous |

The results show that on human tumor cells compound of formula (I) can be effectively combined with platinum-containing compound cisplatin, producing synergic effect also in this cell line.

Example 4

In vitro Cytotoxic Activity of the Combination with SN-38

SN38 is the active metabolite of irinotecan, from which is obtained by hydrolysis. The results obtained with the drugs as single agents and in combination in Mcf-7 cell line are shown in table 4.

TABLE 4

| | in vitro combination with SN-38 | | | | | |
|---|---|---|---|---|---|---|
| Ratio | $IC_{50}$ (µM) Compound of formula (I) | $IC_{50}$ (µM) SN38 | $IC_{50}$ (µM) Combination | Combination index at 50% inhibition | Combination index at 70% inhibition | Schedule |
| 50:1 | 0.77 | 0.024 | 0.11 | 0.24 | 0.22 | Sequential: SN38 24 hours before compound of formula (I) |
| 25:1 | 0.77 | 0.024 | 0.18 | 0.58 | 0.57 | Sequential: SN38 24 hours before compound of formula (I) |
| 12.5:1 | 0.77 | 0.024 | 0.14 | 0.66 | 0.58 | Sequential: SN38 24 hours before compound of formula (I) |
| 100:1 | 0.77 | 0.024 | 0.22 | 0.40 | 0.28 | Sequential: SN38 24 hours before compound of formula (I) |

The results show that on human tumor cells compound of formula (I) can be effectively combined with the topoisomerase I inhibitor SN-38, producing a strong synergic effect.

Example 5

In vitro Cytotoxic Activity of the Combination with Etoposide

The results obtained with the drugs as single agents and in combination in Mcf-7 cell line are shown in table 5.

TABLE 5

| | in vitro combination with etoposide | | | | | |
|---|---|---|---|---|---|---|
| Ratio | $IC_{50}$ (µM) Compound of formula (I) | $IC_{50}$ (µM) etoposide | $IC_{50}$ (µM) Combination | Combination index at 50% inhibition | Combination index at 70% inhibition | Schedule |
| 0.1:1 | 1.11 | 12.7 | 2.89 | 0.49 | 0.34 | Sequential: etoposide 24 hours before compound of formula (I) |
| 0.05:1 | 1.11 | 12.7 | 4.11 | 0.54 | 0.44 | Sequential: etoposide 24 hours before compound of formula (I) |

TABLE 5-continued in vitro combination with etoposide

| Ratio | IC$_{50}$ (μM) Compound of formula (I) | IC$_{50}$ (μM) etoposide | IC$_{50}$ (μM) Combination | Combination index at 50% inhibition | Combination index at 70% inhibition | Schedule |
|---|---|---|---|---|---|---|
| 0.025:1 | 1.11 | 12.7 | 6.18 | 0.67 | 0.44 | Sequential: etoposide 24 hours before compound of formula (I) |
| 0.2:1 | 1.11 | 12.7 | 3.08 | 0.76 | 0.37 | Sequential: etoposide 24 hours before compound of formula (I) |

The results show that on human tumor cells compound of formula (I) can be effectively combined with etoposide, producing a synergic effect.

Example 6

In vitro Cytotoxic Activity of the Combination with Paclitaxel

The results obtained with the drugs as single agents and in combination in Mcf-7 cell line are shown in table 6.

TABLE 6 in vitro combination with paclitaxel

| Ratio | IC$_{50}$ (μM) Compound of formula (I) | IC$_{50}$ (μM) paclitaxel | IC$_{50}$ (μM) Combination | Combination index at 50% inhibition | Combination index at 70% inhibition | Schedule |
|---|---|---|---|---|---|---|
| 50:1 | 0.67 | 0.008 | 0.103 | 0.43 | 0.47 | Sequential: paclitaxel 24 hours before compound of formula (I) |
| 12.5:1 | 0.67 | 0.008 | 0.065 | 0.73 | 0.69 | Sequential: paclitaxel 24 hours before compound of formula (I) |
| 100:1 | 0.67 | 0.008 | 0.169 | 0.51 | 0.44 | Sequential: paclitaxel 24 hours before compound of formula (I) |

The results show that on human tumor cells compound of formula (I) can be effectively combined with compound paclitaxel, producing a synergic effect.

Example 7

In vitro Cytotoxic Ativity of the Cmbination with Erlotinib

The results obtained with the drugs as single agents and in combination in Mcf-7 cell line are shown in table 7.

TABLE 7 in vitro combination with erlotinib

| Ratio | IC$_{50}$ (µM) Compound of formula (I) | IC$_{50}$ (µM) erlotinib | IC$_{50}$ (µM) Combination | Combination index at 50% inhibition | Combination index at 70% inhibition | Schedule |
|---|---|---|---|---|---|---|
| 0.25:1 | 1.87 | 74.76 | 4.57 | 0.56 | 0.49 | Sequential: erlotinib 24 h before compound of formula (I) |
| 0.125:1 | 1.87 | 74.76 | 7.90 | 0.61 | 0.43 | Sequential: erlotinib 24 h before compound of formula (I) |
| 0.062:1 | 1.87 | 74.76 | 10.63 | 0.51 | 0.67 | Sequential: erlotinib 24 h before compound of formula (I) |

The results show that on human tumor cells compound of formula (I) can be effectively combined with erlotinib, producing a synergic effect.

Example 8

In vitro Cytotoxic Activity of the Combination with Bortezomib

The results obtained with the drugs as single agents and in combination in Mcf-7 cell line are shown in table 8.

TABLE 8 in vitro combination with bortezomib

| Ratio | IC$_{50}$ (µM) Compound of formula (I) | IC$_{50}$ (µM) bortezomib | IC$_{50}$ (µM) Combination | Combination index at 50% inhibition | Combination index at 70% inhibition | Schedule |
|---|---|---|---|---|---|---|
| 50:1 | 0.767 | 0.011 | 0.150 | 0.50 | 0.20 | Sequential: bortezomib 24 h before compound of formula (I) |
| 25:1 | 0.767 | 0.011 | 0.114 | 0.58 | 0.26 | Sequential: bortezomib 24 h before compound of formula (I) |
| 12.5:1 | 0.767 | 0.011 | 0.081 | 0.67 | 0.27 | Sequential: bortezomib 24 h before compound of formula (I) |

The results show that on human tumor cells compound of formula (I) can be effectively combined with bortezomib, producing synergic or strong synergic effect.

Example 9

In vitro Cytotoxic Activity of the Combination with Bortezomib

The results obtained with the drugs as single agents and in combination in the HCT116 human colon carcinoma cell line are shown in Table 9.

TABLE 9 in vitro combination with bortezomib

| Ratio | IC$_{50}$ (μM) Compound of formula (I) | IC$_{50}$ (μM) bortezomib | IC$_{50}$ (μM) Combination | Combination index at 70% inhibition | Combination index at 90% inhibition | Schedule |
| --- | --- | --- | --- | --- | --- | --- |
| 20:1 | 0.80 | 0.009 | 0.08 | 0.56 | 0.56 | Sequential: bortezomib 24 hours before compound of formula (I) |
| 40:1 | 0.80 | 0.009 | 0.18 | 0.69 | 0.61 | Sequential: bortezomib 24 hours before compound of formula (I) |
| 80:1 | 0.80 | 0.009 | 0.28 | 0.68 | 0.56 | Sequential: bortezomib 24 hours before compound of formula (I) |
| 160:1 | 0.80 | 0.009 | 0.37 | 0.64 | 0.51 | Sequential: bortezomib 24 hours before compound of formula (I) |

The results show that on human tumor cells compound of formula (I) can be effectively combined with bortezomib, producing synergic effect.

Example 10

In vitro Cytotoxic Activity of the Combination with ABT-263

The results obtained with the drugs as single agents and in combination in the L-363 human Multiple Myeloma cell line are shown in Table 10.

TABLE 10 in vitro combination with ABT-263

| Ratio | IC$_{50}$ (μM) Compound of formula (I) | IC$_{50}$ (μM) ABT-263 | IC$_{50}$ (μM) Combination | Combination index at 50% inhibition | Combination index at 70% inhibition | Schedule |
| --- | --- | --- | --- | --- | --- | --- |
| 0.05:1 | 0.38 | 7.3 | 2.04 | 0.59 | 0.76 | Simultaneous |
| 0.2:1 | 0.38 | 7.3 | 1.10 | 0.67 | 0.74 | Simultaneous |
| 0.4:1 | 0.38 | 7.3 | 0.71 | 0.64 | 0.64 | Simultaneous |

The results show that on human tumor cells compound of form la (I) can be effectively combined with ABT-263, producing synergic effect.

Example 11

In vitro Cytotoxic Activity of the Combination with Dacarbazine

The results obtained with the drugs as single agents and in combination in the A375 human melanoma cell line are shown in Table 11 and in Table 12.

TABLE 11 in vitro combination with dacarbazine

| Ratio | $IC_{50}$ (μM) Compound of formula (I) | $IC_{50}$ (μM) dacarbazine | $IC_{50}$ (μM) Combination | Combination index at 50% inhibition | Combination index at 70% inhibition | Schedule |
|---|---|---|---|---|---|---|
| 0.025:1 | 1.21 | 37 | 7.04 | 0.35 | 0.42 | Sequential: dacarbazine 24 hours before compound of formula (I) |
| 0.05:1 | 1.21 | 37 | 8.62 | 0.64 | 0.79 | Sequential: dacarbazine 24 hours before compound of formula (I) |
| 0.1:1 | 1.21 | 37 | 6.89 | 0.77 | 0.77 | Sequential: dacarbazine 24 hours before compound of formula (I) |
| 0.2:1 | 1.21 | 37 | 3.56 | 0.61 | 0.64 | Sequential: dacarbazine 24 hours before compound of formula (I) |

TABLE 12 in vitro combination with dacarbazine

| Ratio | $IC_{50}$ (μM) Compound of formula (I) | $IC_{50}$ (μM) dacarbazine | $IC_{50}$ (μM) Combination | Combination index at 50% inhibition | Combination index at 70% inhibition | Schedule |
|---|---|---|---|---|---|---|
| 0.0125:1 | 0.86 | 83 | 16.5 | 0.48 | 0.59 | Simultaneous |
| 0.025:1 | 0.86 | 83 | 15.6 | 0.71 | 0.74 | Simultaneous |
| 0.05:1 | 0.86 | 83 | 10.7 | 0.79 | 0.69 | Simultaneous |
| 0.1:1 | 0.86 | 83 | 5.3 | 0.65 | 0.63 | Simultaneous |

The results show that on human tumor cells compound of formula (I) can be effectively combined with dacarbazine, producing synergic effect using a simultaneous or a sequential schedule of treatment.

Example 12

In vivo Cytotoxic Activity of the Combination of a Compound of Formula (I) with Bevacizumab CD-1 Nu/Nu female mice were obtained from Charles River, Italy. The animals were maintained in cages using steam autoclaved (sterile) bedding, sterilized diet and water were offered ad libitum. MX-1 human breast carcinoma (from American Type Culture Collection) was maintained by subcutaneous (SC) transplantation in athymic mice. Viable MX-1 tumor fragments (weighting 20-30 mg) were obtained aseptically from stock tumors and transplanted subcutaneously by trocar implantation into the left flank of athymic nude mice. Animals were examined regularly for the appearance of tumors. The treatment started when tumors were palpable. Compound of formula (I) was administered by oral route in a volume of 10 ml/kg at the daily dose of 20 mg/kg on days 2, 4, 6, 8, 10 and 12. Bevacizumab was administered by intravenous route at the dose of 20 mg/kg on days 1, 5, 9 and 13. When combined, compound of formula (I) was administered on days 2, 4, 6, 8, 10 and 12 and bevacizumab on days 1, 5, 9 and 13. Tumor growth and body weight were measured every 3 days. Tumor growth was assessed by caliper. The two diameters were recorded and the tumor weight was calculated according the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction. The results are reported in table 13.

TABLE 13

| Treatment | T-C (days) | Toxicity |
|---|---|---|
| Compound of formula (I) 20 mg/kg* | 13 | 0/7 |
| Bevacizumab 20 mg/kg** | 13 | 0/7 |
| Bevacizumab 20 mg/kg + Compound of formula (I) 20 mg/kg*** | 24 | 0/7 |

*Oral treatments made on day 2, 4, 6, 8, 10, 12.
**Treatments made by intravenous route on days 1, 5, 9, 13.
***Compound of formula (I) treatments days: 2, 4, 6, 8, 10, 12 bevacizumab treatments days: 1, 5, 9, 13.
The T-C observed when compound of formula (I) was combined with bevacizumab was similar to the expected by the simple addition of T-C obtained by the single treatments indicating additivity. No toxicity was observed in any of the treatment group.

Example 13

In vivo Cytotoxic Activity of the Combination of a Compound of Formula (I) with Irinotecan Balb, Nu/Nu male mice, from Harlan (Italy), were maintained in agreement with the European Communities Council Directive no. 86/609/EEC, in cages with paper filter cover, food and bedding sterilized and acidified water. Fragments of HCT-116 human colon cancer tumors were implanted subcutaneously. The treatment started when tumors were palpable. Compound of formula (I) was administered by oral route at the daily doses of 20 mg/kg daily on day 2, 4, 6, 8, 10, 12. Irinotecan was administered by intravenous route at the dose of 45 mg/kg on days 1, 5, 9. When combined, compound of formula (I) was administered on day 2,4,6,8,10,12 and irinotecan on days 1, 5, 9. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1g). Toxicity was evaluated on the basis of body weight reduction. The results are reported in table 14.

TABLE 14

| Treatment | T-C (days) | Toxicity |
|---|---|---|
| Compound of formula (I) 20 mg/kg | 4 | 0/7 |
| irinotecan 45 mg/kg** | 18 | 0/7 |
| irinotecan 45 mg/kg + Compound of formula (I) 20 mg/kg*** | 25 | 0/7 |

*Oral treatments made on days 2, 4, 6, 8, 10, 12
**Treatments made by intravenous route on days 1, 5, 9
***Compound of formula (I) treatments days: 2, 4, 6, 8, 10, 12 irinotecan treatments days: 1, 5, 9.
The T-C observed when compound of formula (I) was combined with irinotecan was superior to the expected by the simple addition of T-C obtained by the single treatments indicating synergism.

Example 14

In vivo Cytotoxic Activity of the Combination of a Compound of Formula (I) with Docetaxel CD1 Nu/Nu female mice were obtained from Charles River, Italy, The animals were maintained in cages using steam autoclaved (sterile) bedding, sterilized diet and water were offered ad libitum. MX-1 human breast carcinoma (from American Type Culture Collection) was maintained by subcutaneous (SC) transplantation in athymic mice. Viable MX-1 tumor fragments (weighting 20-30 mg) were obtained aseptically from stock tumors and transplanted subcutaneously by trocar implantation into the left flank of athymic nude mice. Animals were examined regularly for the appearance of tumors. When treatment starts the mean tumor volume was about 110 mm$^3$.

Compound of formula (I) was administered by oral route at the dose of 20 mg/kg daily on day 2, 4, 6, 9, 11, 13. Docetaxel was administered by intravenous route at the dose of 5 mg/kg on days 1, 8, 15. When combined, compound of formula (I) was administered on day 2, 4, 6, 9, 11, 13 and docetaxel on days 1, 8, 15. Tumor growth and body weight were measured every 3 days, Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction. The results are reported in table 15.

TABLE 15

| Treatment | T-C (days) | Toxicity |
|---|---|---|
| Compound of formula (I) 20 mg/kg | 10 | 0/7 |
| docetaxel 5 mg/kg** | 9 | 0/7 |
| docetaxel 5 mg/kg + Compound of formula (I) 20 mg/kg*** | >100 | 1/7 |

*Oral treatments made on day 2, 4, 6, 9, 11, 13
**Treatments made by intravenous route at days 1, 8, 15
***Compound of formula (I) treatments days: 2, 4, 6, 9, 11, 13 docetaxel treatments days: 1, 8, 15.
The T-C observed when compound of formula (I) was combined with docetaxel was superior to the expected by the simple addition of T-C obtained by the single treatments indicating strong synergism. After 120 days of observation, animals were still tumor free.

The invention claimed is:

1. A therapeutic combination comprising (a) a compound of formula (I):

formula (I):

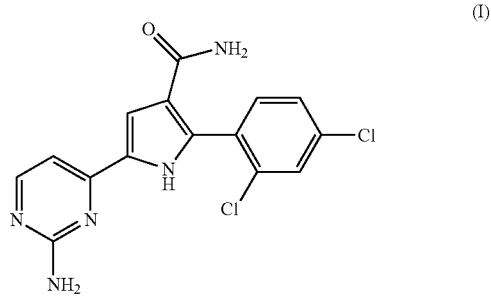 [SMILES: NC(=O)c1cc(-c2ccnc(N)n2)[nH]c1-c1ccc(Cl)cc1Cl]

(I)

and (b) paclitaxel wherein (a) or (b) are present in each case in free form or in the form of a pharmaceutically acceptable salt or any hydrate thereof, wherein the ratio of (a) to (b) is selected from the group consisting of 12.5:1, 50:1 and 100:1.

2. The combination according to claim 1 which is a combined preparation for simultaneous, separate or sequential use.

3. A pharmaceutical composition comprising a combination according to claim 1 admixed with a pharmaceutically acceptable carrier, diluent or excipient.

4. A commercial package comprising, in a suitable container mean, (a) a compound of formula (I) as defined in claim 1, and (b) paclitaxel wherein (a) or (b) are present in each case in free form or in the form of a pharmaceutically acceptable salt or any hydrate thereof, together with instructions for simultaneous, separate or sequential use thereof, wherein the ratio of (a) to (b) is selected from the group consisting of 12.5:1, 50:1 and 100:1.

* * * * *